United States Patent [19]

Kado et al.

[11] Patent Number: 5,332,667
[45] Date of Patent: Jul. 26, 1994

[54] METHOD FOR PRODUCING BIOLOGICALLY ACTIVE POLYSACCHARIDE RON SUBSTANCE

[75] Inventors: Hisao Kado; Yasuo Yoneta; Suguru Takeo; Yutaka Mitani; Nobuhiro Watanabe, all of Yaizu, Japan

[73] Assignee: Sapporo Breweries Limited, Tokyo, Japan

[21] Appl. No.: 116,210

[22] Filed: Sep. 2, 1993

Related U.S. Application Data

[63] Continuation of Ser. No. 912,204, Jul. 10, 1992, abandoned, which is a continuation of Ser. No. 807,968, Dec. 11, 1991, abandoned, which is a continuation of Ser. No. 469,298, Jan. 24, 1990, abandoned.

[30] Foreign Application Priority Data

Feb. 8, 1989 [JP] Japan .................. 1-29381

[51] Int. Cl.$^5$ .................... C12N 1/20; C12P 19/04
[52] U.S. Cl. .................... 435/101; 435/183; 435/252.1; 435/822; 536/1.11; 536/55.1; 536/127; 536/123.12
[58] Field of Search .................... 435/101, 183, 252.1, 435/822; 536/1.1, 55.1

[56] References Cited

U.S. PATENT DOCUMENTS 4,762,825  8/1988  Takeo et al. .................... 514/54

FOREIGN PATENT DOCUMENTS 0087404  8/1983  European Pat. Off. .
0172559  6/1987  European Pat. Off. ............ 435/101
3224547  1/1984  Fed. Rep. of Germany .

OTHER PUBLICATIONS

Gherna et al., ATCC Catalogue of Bacteria & Bacteriophages, 17th edition, 1989, p. 123, American Type Culture Collection.
Marina E. Preobrazhenskaya et al, Studies on Some Biologically Active Dextrans, Carbohydrate Research, 66(1978) pp. 213–223.
S. M. Navashin et al, Antitumor and Antibacterial Activity of Dextran LU-122 and Its Effect on Macrophage Activity, Curr. Chemother. Immunother., Proc. Int. Congr. Chemther, 12th, 1, pp. 190–192 (1982).
Chemical Abstracts, Jan. 2, 1989, vol. 110, 387w, Suguru et al, "Studies of an antitumor Polysaccharide RBS derived from rice bran. II Preparation and general properties of RON, an active fraction of RBS." & Chem. Pharm. Bull. 1988.
Chemical Abstracts, Oct. 29, 1973, vol.79:10174n, OLLE, "Structural studies on the extracellular polysaccharides elatorated by Leoconostoc Mesenteroides NRRL B-512 and Diplococcus pneumoniae Type II" & Chem. Commun. Univ. Stockholm 1973.
Sneath et al. "Bergey's Manual of Systematic Bateriology", 1986, vol. 2. pp. 1071–1075.

*Primary Examiner*—Herbert J. Lilling
*Attorney, Agent, or Firm*—Frishauf, Holtz, Goodman & Woodward

[57] ABSTRACT

A biologically active polysaccharide RON substance which is excellent in such biological activities as antitumor activities, is produced by using a microorganism belonging to the genus Leuconostoc, which has an activity of producing the RON substance.

14 Claims, 3 Drawing Sheets

METHOD FOR PRODUCING BIOLOGICALLY ACTIVE POLYSACCHARIDE RON SUBSTANCE

This application is a continuation of application Ser. No. 07/912,204 filed Jul. 10, 1992, now abandoned which is a continuation of application Ser. No. 07/807,968 filed Dec. 11, 1991 (abandoned), which is a continuation of application Ser. No. 07/469,298 filed Jan. 24, 1990 (abandoned).

BACKGROUND OF THE INVENTION

(1) Field of the Invention

The present invention relates to a process for the preparation of a biologically active polysaccharide RON substance (hereinafter referred to as "RON substance" according to circumstance) having an excellent antitumor activity, an immunomodulating activity and a host defense activity against infectious diseases, which comprises using a microorganism having an activity of producing this biologically active polysaccharide RON substance or a processed culture broth of this microorganism, and also to a novel microorganism having an activity of producing an excellent biologically active polysaccharide RON substance.

(2) Description of the Related Art

The RON substance intended in the present invention and a process for extracting this RON substance from rice bran having already been disclosed in Japanese Patent Publication No. 62-7173 (which corresponds to U.S. Pat. No. 4,762,825).

According to this conventional process, the RON substance is extracted from rice bran and the extract is purified. Therefore, the quality of the starting material is unstable, and there are considerable dispersions of the physical properties and biological activities of the obtained substance. Moreover, the yield is low and many steps are required, and the conventional process involves the problem of long operation time and is economically disadvantageous.

SUMMARY OF THE INVENTION

Under this background, we made an extensive investigation with a view to overcoming the above-mentioned defects of the conventional techniques, and as the result, it was found that a process for producing the RON substance with high efficiency when using a specific microorganisms. Based on these findings, the present invention has been accomplished.

More specifically, in accordance with the present invention, there are provided a methods for the preparation of the RON substance having the following properties. The methods comprise using a microorganism belonging to the genus Leuconostoc, which has an activity of producing the RON substance, using a processed culture broth of this microorganism, and collecting the RON substance from the above-mentioned procedures, and a novel microorganism having an activity of producing the RON substance:

(1) Form: the substance is a white amorphous powder having no taste and no smell;

(2) Solubility: the substance is soluble in water but the solution becomes milky white and viscous when the concentration is elevated, the substance is soluble in formamide and dimethylsulfoxide but the substance is insoluble in alcohols, acetone, benzene, ethyl acetate, hexane, chloroform and carbon tetrachloride;

(3) pH of Aqueous Solution: the aqueous solution is neutral or weakly acidic;

(4) Constituent Saccharide: the substance is composed solely of glucose;

(5) Elementary Analysis Values: the substance comprises 44.0 to 45.0% of C and 6.1 to 6.3% of H;

(6) Structure: the substance is an α-1,6-glucan and containing a small amount of 3,6-branched side chains;

(7) Proteins: the substance contains almost no proteins;

(8) Molecular Weight: the substance does not permeate through a dialysis membrane and the molecular weight is presumed to be higher than 10,000 daltons;

(9) Specific Rotation: $[\alpha]_D^{25} = +190° \sim +220°$ (C=0.5, formamide);

(10) Color Reaction: the substance is positive to anthrone sulfuric acid reaction and phenol sulfuric acid reaction but negative to the biurette reaction, the Lowry-Folin reaction, the Elson-Morgan reaction and the iodine reaction;

(11) Melting Point: the substance has no definite melting point;

(12) Ultraviolet Absorption Spectrum: the substance has no characteristic absorption;

(13) Infrared Absorption Spectrum: the substance shows a characteristic absorption of α-glucan;

(14) $^{13}C$-NMR Spectrum: the substance shows the characteristic chemical shift values of α-1,6-glucan in the main signals; and (15) Biological Activity: the substance has an antitumor activity.

DETAILED DESCRIPTION OF THE PREFERRED EMBODIMENT

According to the present invention, the RON substance can be obtained by using a microorganism belonging to the genus Leuconostoc and having an ability of producing the RON substance in a culture medium to accumulate the RON substance in the culture broth and then collecting said RON substance. The RON substance can also be obtained by treating a processed culture broth of this microorganism with sucrose to form the biologically active polysaccharide RON substance and then collecting the RON substance.

As specific examples of the microorganism capable of producing the RON substance there can be mentioned *Leuconostoc mesenteroides* subsp. dextranicum, strain BL-75 and strain 46-1 isolated from rice bran etc. The microbiological characteristics of these strains are as follows.

Strain BL-75

Gram stain: +

Morphological characteristics: spherical to ellipsoidal, 0.4 to 0.7 μm, chain of 3 to 4 cocci, formation of cluster Catalase reaction: −

Oxidase reaction: −

Free oxygen demand: facultative anaerobic

Decomposition of arginine: −

Lactic acid fermentation: hetero type, D-lactic acid
Production of acid from carbohydrates:
  arabinose: −
  fructose: +
  galactose: +
  glucose: +
  lactose: +
  mannose: +
  trehalose: +
Hydrolysis of esculin: +
Production of dextran: +
Growth in the presence of NaCl:
  3.0% NaCl: +
  6.5% NaCl: −
Growth at different initial pH values:
  pH 4.8: −
  pH 6.5: +
Final pH in glucose medium: 4.3

Strain 46-1

Gram stain: +
Morphological characteristics: spherical to ellipsoidal, 0.4 to 0.6 μm, pair and short chain
Catalase reaction: −
Oxidase reaction: −
Free oxygen demand: facultative anaerobic
Decomposition of arginine: −
Lactic acid fermentation: hetero type, D-lactic acid
Production of acid from carbohydrates:
  arabinose: −
  fructose: +
  galactose: +
  glucose: +
  lactose: +
  mannose: +
  trehalose: +
Hydrolysis of esculin: +
Production of dextran: +
Growth in the presence of NaCl:
  3.0% NaCl: +
  6.5 % NaCl: −
Growth at different initial pH values:
  pH 4.8: +
  pH 6.5: +
Final pH in glucose medium: 4.1

In view of the foregoing, the mycological properties of both strains are summarized as follows.

1. Both strains are positive to the Gram stain and are facultative anaerobic.

2. The morphological characteristics is in a chain of spherical to ellipsoidal cocci.

3. Both strains are positive to the production of acid from carbohydrates except arabinose.

4. The lactic acid fermentation is of the hetero type, and only the D-form of lactic acid is formed.

5. Both strains are negative to the decomposition of arginine.

With reference to Bergey's Manual of Determinative Bacteriology, 8th edition, it was judged that the strain BL-75 belonged to the genus Leuconostoc, and since the strain was positive to the production of dextran and negative to the production of an acid from arabinose and the strain did not grow in the presence of 6.5% NaCl, therefore, the strain BL-75 was identified as a strain of Leuconostoc dextranicum and deposited as FERM BP-2242 in the Fermentation Research Institute, Agency of Industrial Science and Technology, Ministry of International Trade and Industry.

Afterward, we learned by reading after described new handbooks that the name of the species of Leuconostoc dextranicum was changed. Accordingly, the strain BL-75 and the strain 46-1 found afterward were investigated again with reference to Bergey's Manual of Systematic Bacteriology, Vol. 2, 9th edition(1986) and Methods in Microbiology, Vol. 16, pages 147 and 148 (1984). As the result, both the strains were identified as the strains of Leuconostoc mesenteroides subsp. dextranicum. Accordingly, we changed the name of strain BL-75 to Leuconostoc mesenteroides subsp. dextranicum, BL-75, and strain 46-1 was named Leuconostoc mesenteroides subsp. dextranium, 46-1 and the latter was also deposited as FERM BP-2670 with Fermentation Research Institute, Agency of Industrial Science and Technology, Ministry of International Trade and Industry.

We further searched for the RON substance-producing microorganisms, and it was found that some known strains had an activity of producing the RON substance as well as the strains BL-75 and 46-1. Namely, Leuconostoc mesenteroides subsp. dextranicum, strain NCFB 517 (FERM BP-2711),. strain NCFB 531 (FERM BP-2712), strain NCFB 861 (FERM BP-2713), strain NCFB 864 (FERM BP-2714), strain NCFB 880 (FERM BP-2715), strain ATCC 1956 and strain IFO 3349 were found to be the RON substance producers.

Accordingly, any of the microorganisms belonging to the genus Leuconostoc and being capable of producing the RON substance can be utilized for the production of the RON substance of the present invention.

Culture of the microorganism capable of producing the RON substance is, in principle, carried out according to an ordinary microorganism-culture method. Since the microorganism belonging to the genus Leuconostoc is facultative anaerobic and it demands no oxygen, stationary culture using a liquid medium or gently agitating culture to unify the temperature distribution is generally advantageously adopted.

In the case of obtaining the RON substance directly by using a method of direct culturing, in the culture medium used for culturing, sucrose should be indispensably contained as the carbon source for producing the RON substance. Any of synthetic culture media, semi-synthetic culture media and natural media can be used, so far as other carbon source, a nitrogen source, an inorganic substance and other nutrient sources that can be utilized by the above-mentioned microorganism are contained in addition to sucrose. Any of crude and refined products of sucrose can be optionally used. For example, first-class white refined sugar, muscovado, theriac, blackstrap molasses or sucrose of the reagent grade can be used. A sucrose concentration of about 0.5 to about 70%, preferably 5 to 50% is preferable. As the nitrogen source, there can be used yeast extract, peptone, gluten meal, soybean powder, corn steep liquor, dry yeast, meat extract, ammonium sulfate and urea singly or mixture thereof to the medium in an amount of 0.5 to 5%, preferably 1 to 3%. As the inorganic substance, there can be used phosphoric acid salts and salts of metals such as magnesium, manganese, iron, cobalt and sodium can be appropriately added.

The incubation temperature may be one for mesophiles, therefore, it is generally 15° to 45° C., preferably 20° to 30° C. The pH in culturing is 5 to 7. The incubation time is generally 5 to 96 hours, preferably 10 to 24 hours. The RON substance can be produced in the medium as described above.

In the case where the RON substance is obtained by using the processed culture broth of the microorganism, in order to accumulate the RON substance in the above mentioned culture broth, it is indispensable that sucrose should be contained as the carbon source in the culture medium. It is preferred that the sucrose concentration is 0.1 to 10%, especially 1 to 5%. Other conditions such as the culturing pH value, the culturing temperature and the culturing time are the same as those described above with respect to the direct preparation of the RON substance by the culturing of the microorganism.

As the processed culture broth of the microorganism, there can be mentioned a supernatant obtained by subjecting a culture broth of a microorganism having an activity of producing the RON substance to centrifugal separation or the like, a product obtained by pulverizing cells of the culture broth by ultrasonic pulverizer, if necessary removing insoluble substances by centrifugal separation or the like, and a product obtained by dialyzing the above-mentioned processed culture broth at 0° to 30° C. for 5 to 72 hours against a buffer solution having a pH value of 5 to 7, by using a dialysis membrane. The RON substance can be formed by reacting the above-mentioned processed culture broth with sucrose. The reaction temperature is 20° to 45° C., preferably 25° to 35° C., and the reaction time is 5 to 50 hours and the pH value is 5 to 7.

The produced RON substance is usually contained in the culture broth or reaction mixture. After the cells and insoluble substances are moved by centrifugal separation, filtration or the like, the RON substance can be collected by carrying out precipitation with a polar organic solvent such as methanol, ethanol, propanol, butanol or acetone and/or salting-out with ammonium sulfate, or repeating these operations. Furthermore, dialysis, gel filtration, ultrafiltration and a treatment with an ion exchange resin or active carbon are carried out singly or in combination, whereby the RON substance having an enhanced purity can be obtained. Moreover, a white powder of the RON substance can be obtained by a spray drying, freeze drying or precipitation with a polar organic solvent and subsequent drying. Still further, the RON substance can be prepared more efficiently by using a bioreactor involving the above-mentioned microorganisms.

The properties of the so-obtained RON substance are as follows.

(1) Form: the substance is a white amorphous powder having no taste and no small;

(2) Solubility: the substance is soluble in water but the solution becomes milky white and viscous when the concentration is elevated, the substance is soluble in formamide and dimethylsulfoxide but the substance is insoluble in alcohols, acetone, benzene, ethyl acetate, hexane, chloroform and carbon tetrachloride;

(3) pH of Aqueous Solution: the 1% aqueous solution is neutral or weakly acidic;

(4) Constituent Saccharide: the substance is composed solely of glucose as described below. When the present substance was completely hydrolyzed with sulfuric acid and formic acid and the hydrolysis product was analyzed by the thin layer chromatography and high-performance liquid chromatography under conditions described below, a saccharide other than glucose could not be confirmed.

(1) Thin layer chromatography

Carrier: Silica Gel HP-K ® supplied by Wattman
Developing solvent: butanol/acetic acid/water (2/1/1)

(2) High-performance liquid chromatography

Column: YMC PA-03 ® supplied by Yamamura Kagaku
Developing solvent: water/acetonitrile (30/70)

Accordingly, it is obvious that the present substance is a polysaccharide comprising only glucose as the constituent saccharide.

(5) Elementary Analysis Values: the substance comprises 44.0 to 45.0% of C, 6.1 to 6.3% of H and 0.1% of ash.

(6) Structure

Figure 1:
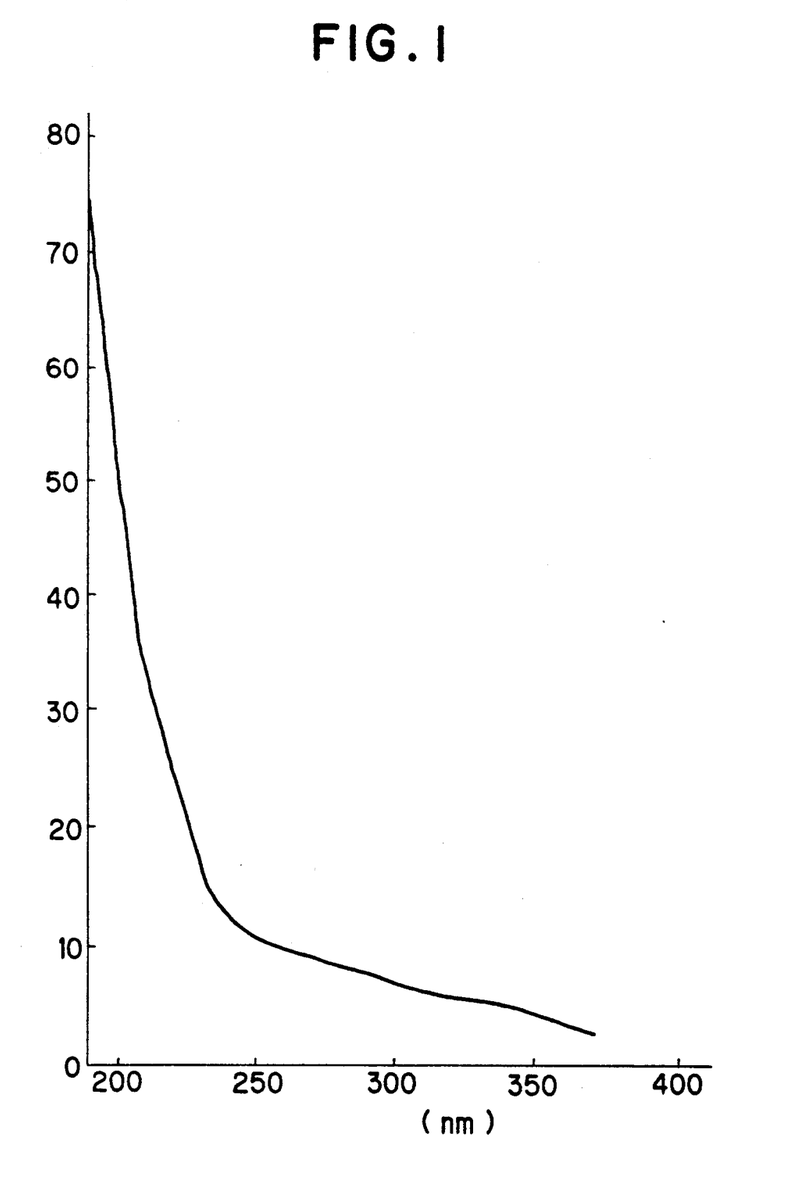
FIG. 1 shows the ultraviolet absorption spectrum of the RON substance obtained by the present invention.
Figure 2:
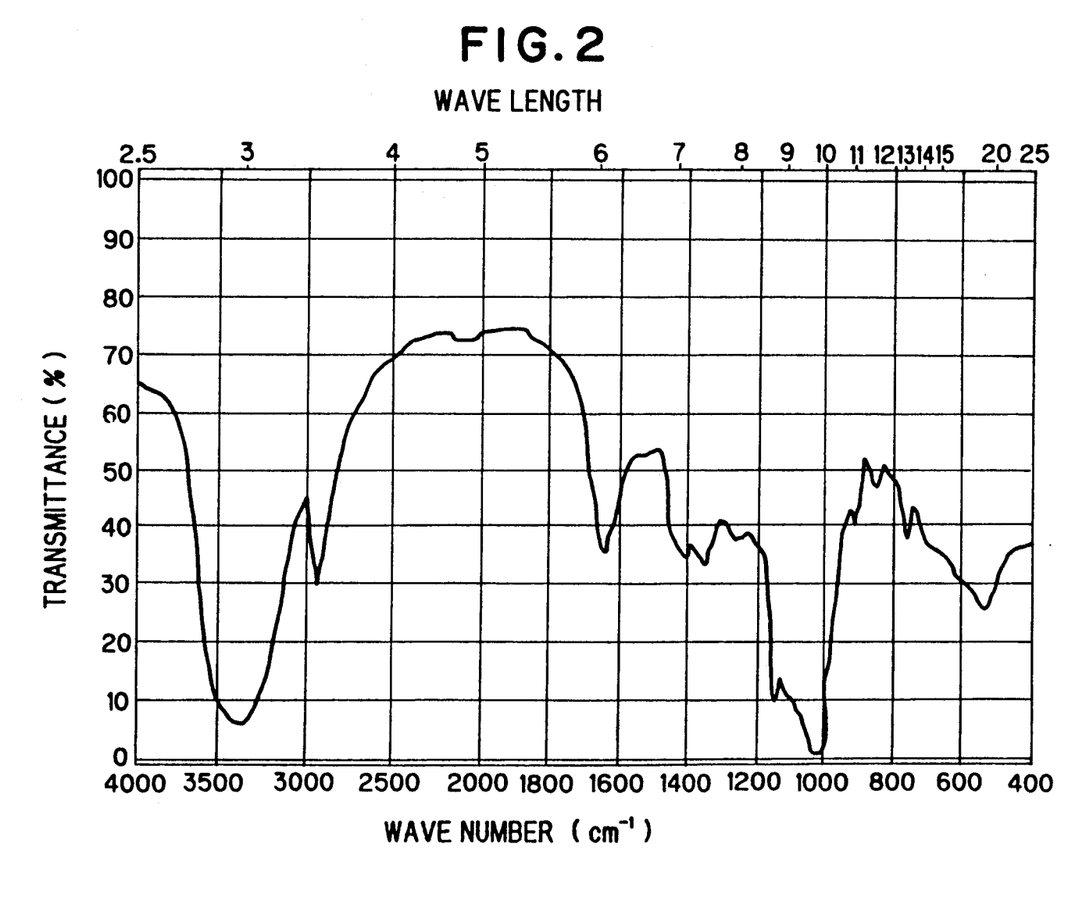
FIG. 2 shows the infrared absorption spectrum of the RON substance.
Figure 3:
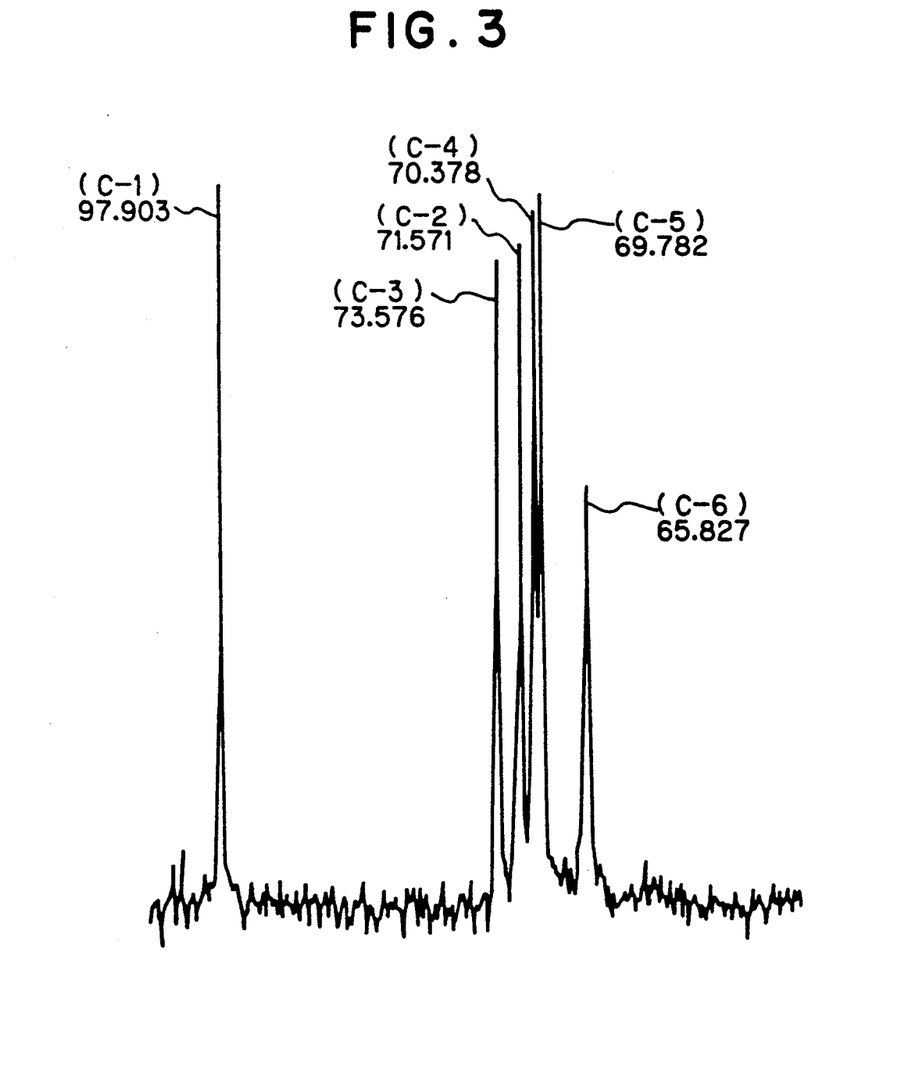
FIG. 3 shows the $^{13}C$-NMR spectrum of the RON substance.

The present substance shows characteristic absorptions in the ultraviolet absorption spectrum as shown in FIG. 1, and the present substance shows characteristic absorptions of α-glucan in the infrared absorption spectrum as shown in FIG. 2. Moreover, the present substance shows the characteristic peak of α-1,6-glucan as the main signals in the 13C-NMR spectrum as shown in FIG. 3.

From these data mentioned above, it is confirmed that the present substance is an α-glucan. Moreover, in the periodic acid oxidation test, the present substance consumes about 1.9 moles of periodic acid per glucose residue to form about 0.98 mole of formic acid, and in the Smith degradation, a large quantity of glycerol is detected. Accordingly, it is presumed that the present substance has a large amount of 1→6 glucosidic bonds. In order to know a more detailed structure, the present substance was completely methylated and hydrolyzed, and the obtained methyl saccharide was analyzed. As the result, a large amount of 2,3,4-tri-o-methylglucose, a small amount of 2,3,4,6-tetra-o-methylglucose and 2,4-di-o-methylglucose were found. Accordingly, it is presumed that the RON substance obtained by the process of the present invention is an α-1,6-glucan, having a small amount of 3,6-branched side chains and containing glucose as the sole constituent saccharide, and the present substance has the following skeleton:

wherein Glcp represents glucopyranose, and p and q are numbers of from 0 to 50, with the proviso that the requirement of $p+q \leq 50$ is satisfied.

Proteins: the substance contains almost no proteins;

Molecular Weight: the substance does not permeate through a dialysis membrane and the molecular weight is presumed to be higher than 10,000 daltons;

Specific Rotation: $[\alpha]_D^{25} = +190° \sim +220°$ (C=0.5, formamide);

Color Reaction: the substance is positive to anthrone sulfuric acid reaction and phenol sulfuric acid reaction but negative to the biurette reaction, the Lowry-Folin reaction, the Elson-Morgan reaction and the iodine reaction;

Melting Point: the substance has no definite melting point, and the present substance is browned at 220° C. and blackened at 280° C. to cause carbonization.

Ultraviolet Absorption Spectrum: the substance has no characteristic absorption as shown in FIG. 1;

Infrared Absorption Spectrum: the substance shows characteristic absorption of α-glucan as shown in FIG. 2;

$^{13}$C-NMR Spectrum: the substance shows characteristic chemical shift values of α-1,6-glucan in the main signals as shown in FIG. 3; and Biological Activity: the substance has an antitumor activity.

The RON substance obtained by the present invention can be converted to a substance having a lower molecular weight by adding several percents of sulfuric acid, hydrochloric acid or formic acid to the present substance and gently heating the mixture to effect partial hydrolysis. The molecular weight of the molecular weight-reduced RON substance can be unified by gel filtration using Sepharose®, Sephadex® or Toyopearl® or ultrafiltration having various exclusion limits after the neutralization.

It was found that the RON substance and the low-molecular-weight product of the RON substance having a molecular weight higher than about 10000 obtained according to the present invention had various biological activities such as an antitumor activity, an immunomodulating activity and a host defense activity against infectious diseases. The methods for testing these biological activities and the results obtained when the RON substance obtained in Example 1, the low-molecular-weight product of the RON $F_1$ (having a molecular weight higher than 1,000,000), $F_2$ (having a molecular weight of 100,000 to 1,000,000) and $F_3$ (having a molecular weight of 10,000 to 100,000) prepared from RON obtained in Example 4 by partial hydrolysis using 2% sulfuric acid given hereinafter was administered are described in detail.

(1) Antitumor Activities (a) Effect of Intraperitoneal Administration of the RON Substance against Syngeneic Tumor Meth-A To the peritoneal cavities of 6-week-old female BALB/C-CRJ mice having an average body weight of 20 g, Meth-A tumor cells subcultured in the peritoneal cavities of the same syngeneic mice were transplanted at a rate of $1 \times 10^5$ cells per mouse. The mice were divided into one control group consisting of 20 mice and three test groups, each consisting of 10 mice. Continuously for 5 days from the day subsequent to the transplantation of the tumor cells, 0.1 ml each of physiological saline solutions containing 10 mg, 30 mg and 100 mg of RON per kg of the body weight of one mouse were administered intraperitoneal by cavities to the mice of test groups, respectively, and only a physiological saline solution alone was similarly administered to the mice of the control group. Then, the survival days were observed, and the prolongation of life was calculated according to the following formula:

$$\text{Prolongation of life (\%)} = \frac{\text{average survival time (days) for test group}}{\text{average survival time (days) for control group}} \times 100$$

(b) Effect of Oral Administration of the RON Substance against Syngeneic Tumor Meth-A In the auxillary regions of 6-week-old female BALB/C-CRJ mice having an average body weight of 20 g, Meth-A tumor cells were subcutaneously transplanted at a rate of $6 \times 10^4$ cells per mouse. The mice were divided into one control group consisting of 20 mice and three test groups, each consisting of 10 mice. Continuously for 10 days from the day subsequent to transplantation of the tumor cells, 0.2 ml each of physiological saline solutions containing 10, 30 and 100 mg of the RON substance per kg of the body weight of one mouse were administered orally by using an oral sonde. Only a physiological saline was similarly administered to the mice of the control group. After 35 days from the transplantation of the tumor cells, each mouse was killed, and the propagated tumor was cut out and the weight was measured. The inhibition ratio was calculated according to the following formula:

$$\text{Inhibition ratio (\%)} = \left(1 - \frac{\text{average tumor weight in test group}}{\text{average tumor weight in control group}}\right) \times 100$$

The antitumor activities of the RON substance tested according to the above-mentioned methods (a) and (b) are shown in Table I.

TABLE I

| Sample | Dose (mg/kg) | Intraperitoneal Administration (a) | | Oral Administration (b) | |
|---|---|---|---|---|---|
| | | average survival time (days) | Prolongation of life (%) | average tumor weight (%) | inhibition ratio (%) |
| control (saline) | — | 19.8 | — | 11.00 | — |
| RON substance | 10 | 32.1 | 162 | 5.98 | 46 |
| RON substance | 30 | >42.0 | >212 | 4.26 | 61 |
| RON substance | 100 | 31.8 | 161 | 5.05 | 54 |

From the results shown in Table I, it can be seen that the RON substance exhibits a strong antitumor activity with the optimum dose of about 30 mg/kg both in the intraperitoneal and in the oral administration.

The same procedure as above described (a) and (b) was carried out using the low-molecular-weight products of RON substance $F_1$, $F_2$ and $F_3$ instead of using the RON. The results are shown in Table II.

TABLE II

| Sample | Dose (mg/kg) | Intraperitoneal Administration (a) | | Oral Administration (b) | |
|---|---|---|---|---|---|
| | | average survival time (days) | Prolongation of life (%) | average tumor weight (%) | inhibition ratio (%) |
| Control (saline) | | 19.8 | — | 11.00 | — |
| $F_1$ | 30 | >42.0 | >212 | 4.39 | 60 |
| $F_2$ | 30 | >42.0 | >212 | 4.28 | 61 |
| $F_3$ | 30 | >42.0 | >212 | 4.79 | 56 |

From the result shown in Table II, it is found that the low-molecular-weight products of the RUN substance have an antitumor activity which is equal with the RUN substance before partial hydrolysis.

Furthermore, it was confirmed that when the RON substance and low-molecular-weight products thereof were intraperitoneally or orally administered at a dose of 10 to 100 mg/kg, activities corresponding to a tumor inhibition ratio of 30 to 70% is attained for the murine syngeneic tumors Lewis lung carcinoma, Melanoma B-16, tumors Sarcoma-180 and Ehrlich ascites tumor. Moreover, it was confirmed that when the RUN substance and low-molecular-weight product thereof were administered to mice in combination with an appropriate primer, the cytotoxicity to L-929 cells and the necrotic activity to Meth-A solid tumor were induced in the serum, and a tumor necrosis factor was self-induced in the living body of a tumor-bearing mice. In view of the fact that the RON substance and low-molecular-weight product thereof have no toxicity at all as described hereinafter, it is considered that the RON substance can be a very effective antitumor agent.

(2) Immunomodulating Activities

(a) Carbon Clearance Test (CCT)

This test is used to examine the effect of enhancing the phagocytic activity of the macrophage. A physiological saline solution containing the RON substance or low-molecular weight products thereof such as $F_1$, $F_2$ and $F_3$ dissolved therein was intraperitonearlly administered for 2 days into one group of six 4-week-old female ICR-CRJ mice having an average body weight of 20 g (only a physiological saline was administered to the control group), and on the third day, 0.25 ml of a carbon solution [prepared by diluting a black ink (Fount India ®) supplied by Perikan Co. ) 5 times with a physiological saline solution] was injected into the tail vein of the mice. Just after the injection and after 10 minutes, 0.025 ml of blood was collected from the venous plexus of the retro-orbit of the mice and suspended and dissolved in 3.5 ml of a 0.01 M solution of sodium carbonate. The absorbance ($OD_{650}$) at 650 nm was measured and the reduction ratio of the carbon concentration in blood was examined. The effect was expressed by the phagocytic index represented by the following formula:

$$\text{Phagocytic index } (K) = \frac{\log C_1 - \log C_2}{T_2 - T_1}$$

wherein $C_1$ represents $OD_{650}$ at $T_1$ and $C_2$ represents $OD_{650}$ at $T_2$.

In case of tumor-bearing mice, 7 days before initiation of administration of the RON substance, $F_1$, $F_2$ or $F_3$ $1 \times 10^7$ of Sarcoma-180 cells were transplanted in the muscle of the hind leg of each mouse, and the test was similarly carried out. The obtained results are shown in Table III. It was found that in case of both normal mice and tumor-bearing mice, the function of the reticuloendothelial system of the mice was enhanced by administration of 10 to 100 mg/kg, especially 30 mg/kg, of the RON substance, $F_1$, $F_2$ or $F_3$. It is clear that the phagocytic activity of the macrophage has been increased.

TABLE III

| Sample | Dose (mg/kg) | Normal Mice phagocytic index | Normal Mice relative value (%) | Tumor-Bearing Mice phagocytic index | Tumor-Bearing Mice relative value (%) |
|---|---|---|---|---|---|
| control (saline) | — | $40.2 \times 10^{-3}$ | 100 | $104 \times 10^{-3}$ | 100 |
| RON substance | 10 | $58.3 \times 10^{-3}$ | 145 | $129 \times 10^{-3}$ | 124 |
| RON substance | 30 | $90.0 \times 10^{-3}$ | 224 | $159 \times 10^{-3}$ | 153 |
| Ron substance | 100 | $77.6 \times 10^{-3}$ | 193 | $146 \times 10^{-3}$ | 140 |
| $F_1$ | 30 | $90.8 \times 10^{-3}$ | 226 | $159 \times 10^{-3}$ | 153 |
| $F_2$ | 30 | $87.2 \times 10^{-3}$ | 217 | $157 \times 10^{-3}$ | 151 |
| $F_3$ | 30 | $89.9 \times 10^{-3}$ | 224 | $160 \times 10^{-3}$ | 154 |

(b) Plaque-Forming Cell Test (PFC)

This test is used to examine the effect of enhancing the antibody-producing ability by activation of B cells of the host among the immunomodulating activities.

A physiological saline solution containing the RON substance or low-molecular-weight products thereof such as $F_1$, $F_2$ and $F_3$ was continuously administered for 3 days intraperitoneally to cavities to one group of six 4-week-old female ICR-CRJ mice having an average body weight of 20 g (only a physiological saline was administered to the control group). On the 4th day and 11th day, $4 \times 10^6$ of sheep erythrocytes were injected into the tail vein, and after 4 days, the plaque-forming ability of the mouse spleen cells was determined according to the Cunningham method.

The obtained results are shown in Table IV. It is seen that the antibody-producing ability is highly enhanced by the administration of 10 to 100 mg/kg of the RON substance, $F_1$, $F_2$ or $F_3$.

TABLE IV

| Sample | Dose (mg/kg) | Sensitization on 4th Day number of plaques per spleen | Sensitization on 4th Day relative value (%) | Sensitization on 11th Day number of plaques per spleen | Sensitization on 11th Day relative value (%) |
|---|---|---|---|---|---|
| control (saline) | — | $3.0 \times 10^4$ | 100 | $2.4 \times 10^4$ | 100 |
| RON substance | 10 | $4.6 \times 10^4$ | 153 | $6.5 \times 10^4$ | 271 |
| RON substance | 30 | $7.6 \times 10^4$ | 253 | $8.9 \times 10^4$ | 311 |
| RON substance | 100 | $7.1 \times 10^4$ | 237 | $8.0 \times 10^4$ | 333 |
| $F_1$ | 30 | $7.7 \times 10^4$ | 257 | $8.8 \times 10^4$ | 367 |
| $F_2$ | 30 | $7.4 \times 10^4$ | 247 | $8.4 \times 10^4$ | 350 |
| $F_3$ | 30 | $7.1 \times 10^4$ | 237 | $8.1 \times 10^4$ | 338 |

(c) Delayed Type Hypersensitivity Reaction (DHR)

This test is used to examine the effect of enhancing the cell-mediated immunity action by the activation of T cells of the host among the immunomodulating activities.

A physiological saline containing the RON substance or low-molecular-weight products such as $F_1$, $F_2$ or $F_3$ was orally administered to one group of six 8-week-old female ICR-CRJ mice having an average body weight of 27 g (only a physiological saline was administered to the control group). On the 4th day after the initiation of administration, a 5% ethanol solution of picryl chloride was coated on the abdominal region which had been shaved to effect the primary sensitization. On the 11th day, a 1% olive oil solution of picryl chloride was coated on the front and back sides of both the ears of each mouse to effect the secondary sensitization. After 24 hours, the ear thickness was measured by a gauge, and the increase of the ear thickness was determined from the difference between the ear thickness before and after the coating. In case of tumor-bearing mice, $1 \times 10^5$ of Sarcoma 180 ascitic tumor cells were transplanted into the peritoneal cavity of the mouse one day before the administration. Then, the test was similarly carried out.

The obtained results are shown in Table V. It is seen that in case of both normal mice and tumor-bearing mice, the cell-mediated immunity action is highly enhanced by the oral administration of 30 to 500 mg/kg of the RON substance, $F_1$, $F_2$ or $F_3$.

TABLE V

| Sample | Dose (mg/kg) | Normal Mice | | Tumor-Bearing Mice | |
|---|---|---|---|---|---|
| | | increase of ear thickness (μm) | relative value (%) | increase of ear thickness (μm) | relative value (%) |
| control (saline) | — | 32.1 | 100 | 39.7 | 100 |
| RON substance | 30 | 75.2 | 234 | 26.4 | 272 |
| RON substance | 100 | 70.2 | 219 | 24.3 | 251 |
| RON substance | 500 | 61.3 | 191 | 20.5 | 211 |
| $F_1$ | 30 | 75.3 | 235 | 25.9 | 267 |
| $F_2$ | 30 | 71.8 | 224 | 25.1 | 259 |
| $F_3$ | 30 | 70.0 | 218 | 25.0 | 258 |

From the results of the immunity action tests (a), (b) and (c), it is seen that various immunity actions in mice having different mechanisms can be conspicuously enhanced by the RON substance and low-molecular-weight products such as $F_1$, $F_2$ and $F_3$. Since an immunomodulating agent is generally used when the immunological competence of a living body is reduced or the foreign antigen-recognizing recognizing function is poor, it is expected that the RON substance and low-molecular-weight products such as $F_1$, $F_2$ and $F_3$ will be effectively used as a therapeutic agent, adjuvant therapeutic agent, combined therapeutic agent, preventing agent or recuperation-accelerating agent after the operation against bacterial and virus infectious diseases and malignant tumors. In addition to the above-mentioned immunity activating and recovering actions, the immunomodulating agent exerts a function of normalizing an abnormally enhanced immunoreaction in a living body, and it is considered that the RON substance and low-molecular-weight products such as $F_1$, $F_2$ and $F_3$ will be applied to self-immunity diseases such as rheumatism, collagen diseases and allergic diseases.

(3) Host Defense Activity

In general, a living body has a sufficient defense activity against the invasion of foreign bacteria. It is known that in the cancer-bearing state, especially at the later stage of cancer, the defense activity is drastically reduced and a serious damage is incurred even by non-pathogenic bacteria ordinarily symbiotic with the host.

Accordingly, in order to examine whether or not the RON substance and low-molecular-weight products such as $F_1$, $F_2$ and $F_3$ can enhance the defense activity of the host against these bacterial infectious diseases, the effect of the RON substance, $F_1$, $F_2$ and $F_3$ on the infection with *Escherichia coli* and *Listeria monocytogenes* was examined.

A physiological saline solution containing 10 to 100 mg/kg of the RON substance, $F_1$, $F_2$ or $F_3$ was administered subcutaneously to the backs of one group of twenty 7-week-old female ICR-CRJ mice having an average body weight of 26 g (only physiological saline was administered to the control group) once one day before the infection with the bacteria and once one day after the infection with the bacteria. In case of *Escherichia coli*, $2 \times 10^7$ of cells were transplanted subcutaneously on the back, and in case of *Listeria monocytogenes*, $2 \times 10^7$ of cells were transplanted intraperitoneally. Then, the mice were observed for 1 week, and the number of survived mice was counted and the protective effect was calculated according to the following formula:

$$\text{Protective effect } (\%) = \frac{(\text{number of survival mice in test group}) - (\text{number of survival mice in control group})}{\text{number of mice in one group}} \times 100$$

The obtained results are shown in Table VI. It is seen that when 10 to 100 mg/kg of the RON substance, $F_1$, $F_2$ or $F_3$ is administered before the infection with *Escherichia coli*, a very strong defense activity against the infection with *Escherichia coli* can be attained, and a significant effect of enhancing the defense activity against the infection with *Listeria monocytogenes*. In case of the administration after the infection, the RON substance has a significant therapeutic effect against both the infectious bacteria.

In view of the fact that the RON substance, $F_1$, $F_2$ and $F_3$ have no toxicity as illustrated hereinafter, it is considered that the RON substance and low-molecular-weight products such as $F_1$, $F_2$ and $F_3$ can be very useful host defense against infectious diseases.

TABLE VI

| Infectious Bacterium | Sample | Dose (mg/kg) | One Day before Infection | | One Day after Infection | |
|---|---|---|---|---|---|---|
| | | | number of survival mice | protective effect (%) | number of survival mice | protective effect (%) |
| *Escherichia coli** | control (saline) | — | 0 | — | 0 | — |
| " | RON substance | 10 | 16 | 80 | 11 | 55 |
| " | RON substance | 30 | 18 | 90 | 14 | 70 |
| " | RON substance | 100 | 18 | 90 | 14 | 70 |
| " | $F_1$ | 30 | 18 | 90 | 14 | 70 |

TABLE VI-continued

| Infectious Bacterium | Sample | Dose (mg/kg) | One Day before Infection | | One Day after Infection | |
|---|---|---|---|---|---|---|
| | | | number of survival mice | protective effect (%) | number of survival mice | protective effect (%) |
| " | F$_2$ | 30 | 17 | 85 | 13 | 65 |
| " | F$_3$ | 30 | 17 | 85 | 11 | 55 |
| Listeria mono-cytogenese** | control (saline) | — | 0 | — | 0 | — |
| " | RON substance | 10 | 7 | 35 | 8 | 40 |
| " | RON substance | 30 | 15 | 75 | 13 | 65 |
| " | RON substance | 100 | 13 | 65 | 12 | 60 |
| " | F$_1$ | 30 | 14 | 70 | 13 | 65 |
| " | F$_2$ | 30 | 14 | 70 | 14 | 70 |
| " | F$_3$ | 30 | 12 | 60 | 12 | 60 |

Note
*Escherichia coli SB-001
**Listeria monocytogenes SB-010

The acute toxicity of the RON substance will now be described. The RON substance, F$_1$, F$_2$ and F$_3$ were orally administered to one group of ten 5-week-old male SD-CRF rats having a body weight of 120 to 150 g at a dose of 15 g/kg, which is a physical administration limit dose, and the rats were observed. None of the rats died, and the increase of the body weight was not different from that in the control group and no abnormality was observed in both appearance and necropsy. Accordingly, it is judged that LD$_{50}$ is larger than 15 g/kg and the RON substance, F$_1$, F$_2$ and F$_3$ have no acute toxicity.

When the RON substance was intravenously injected, LD$_{50}$ was 300 mg/kg, and in case of F$_1$, F$_2$ and F$_3$, the toxicity decreased with decrease of the molecular weight. In case of F$_3$, LD$_{50}$ was larger than 5 g/kg and no toxicity was observed. Accordingly, the molecular weight-reduced. RON substance is very advantageous when used as an injection drug.

According to the present invention, the RON substance having the above-mentioned excellent antitumor activity, immunomodulating activity host defense activity against infections can be obtained stably in a large quantity as a fermentation product by a microorganism, and a pure product can be obtained by relatively easy methods. Accordingly, the present invention makes a great contribution to the technique of producing the present RON substance by using a microorganism on an industrial scale.

Furthermore, the RON substance and low-molecular-weight products thereof have functions of enhancing the cytotoxicity of natural killer cells derived from spleen cells of rats and activating the cytotoxic activity against L-929 cells of resident peritoneal macrophages of a mouse. Moreover, the RON substance has an immunity activating ability and a function of enhancing a production of a cytokine such as interferon, and therefore, it is expected that the RON substance will exert preventive and therapeutic effects against virus diseases such as herpes, influenza and AIDS. Still further, it is considered that the RON substance will be useful as a preventive and therapeutic agent against hepatitis such as chronic hepatitis and liver diseases.

Since the RON substance, F$_1$, F$_2$ and F$_3$ can be orally or non-orally administered, it is expected that the RON substance will be effectively used as an antitumor agent, immunomodulating agent or preventive or therapeutic agent against infectious diseases.

In the practical production of medicines, the RON substance, F$_1$, F$_2$ or F$_3$ is used alone or combined with an excipient (such as water, physiological saline, polyethylene glycol, glycerol, starch, dextrin or lactose) and formed into a liquid preparation, a pill, a tablet, a powder or a suppository.

Since the RON substance has no toxicity, shows various biological activities valuable for the maintenance of health by oral administration, has no taste or smell and can be easily processed, therefore the RON substance can be used as a food or drink for prevention of diseases or maintenance of the health or as an additive to foods or drinks in addition to medicines as mentioned above.

According to the present invention, the RON substance can be stably obtained in a high yield as a fermentation product by a microorganism. There are few of substances having no toxicity and having excellent antitumor activity, immunomodulating activity and host defense activity against infections, like the RON substance obtained according to the present invention. Therefore, the present invention is industrially very advantageous and valuable.

Examples

The present invention will now be described in detail with reference to the following examples that by no means limit the scope of the invention.

EXAMPLE 1

Culturing

Cells obtained by the stab culture of Leuconostoc mesenteroides subsp. dextranicum, BL-75 (FERM BP-2242) were inoculated into 8 ml of a culture medium (comprising 2.0% of sucrose, 0.5% of yeast extract and 2.0% of K$_2$HPO$_4$ and having a pH value of 7.4) charged in a test tube having a diameter of 15 mm. The stationary culture was carried out at 26° C. for 24 hours. Then, 8 ml of the culture broth was charged in an Erlenmeyer flask having a volume of 500 ml, in which 400 ml of the culture medium having the same composition as described above was charged, and the stationary culture was carried out at 26° C. for 24 hours. Then, 400 ml of the culture broth was inoculated in 20 l of SM culture medium (comprising 15% of sucrose, 0.05% of yeast extract, 0.5% of K$_2$HPO$_4$ and 0.1% of NaCl and having a pH value of 7.4), which was charged in a jar fermentator having a volume of 30 l, and cultured at 30° C. for 15 hours under circulation of nitrogen with gentle stirring (0.2 v/v/min, agitation of 10 rpm).

Purification

After the pH value of the obtained culture broth was adjusted to 7, 20 l of the culture broth was heated at 100° C. for the sterilization, and the cells and insoluble substances were removed by continuous centrifugal separator to obtain 18 l of a culture supernatant.

Methanol was gradually added to the obtained culture supernatant so that the final concentration was 40% (v/v), and the mixture was allowed to stand still. The supernatant was removed by decantation and the obtained precipitate was washed with 60% (v/v) methanol. The precipitate was dissolved in 18 l of deionized water, and precipitation with methanol and washing with 60% (v/v) methanol were carried out to obtain 2.8 kg of a glutinous white precipitate. The precipitate was dissolved in 15 l of deionized water, and the solution was spray-dried to obtain 550 g of a white powder of the RON substance.

EXAMPLE 2

Culture and removal of cells by the centrifugal separation and methanol precipitation were carried out in the same manner as described in Example 1 except that 10% of blackstrap molasses was added instead of sucrose to the SM culture medium used in Example 1, whereby about 2.5 kg of a glutinous precipitate was obtained. The obtained precipitate was dissolved in a small amount of deionized water, and the solution was dropped into acetone. The obtained precipitate was vacuum-dried to obtain 490 g of a white powder of the RON substance.

EXAMPLE 3

Methanol was gradually added to 100 ml of the culture supernatant obtained in Example 1 so that the final concentration was 40% (v/v), and the obtained glutinous precipitate was washed with 60% (v/v) methanol and dissolved in 100 ml of deionized water. The solution was applied to DEAE-Toyopearl 650M ® equilibriated with water, and passed fractions were collected and subjected to ultrafiltration with a membrane having a exclusion molecular weight of 100,000, followed by concentration and desalting, and freeze drying, to obtain 2.2 g of a white powder of the RON substance.

EXAMPLE 4

In 100 ml of 2% sulfuric acid was dissolved 2.0 g of the white powder of the RON substance obtained in Example 1, and partial hydrolysis was carried out at 60° C. for 4 hours. The reaction mixture was neutralized with $BaCO_3$, and the precipitate was removed by centrifugal separation. Ultrafiltration was carried out in sequence by membranes having exclusion molecular weights of 1,000,000, 100,000 and 10,000, respectively, to obtain three fractions, that is, fraction $F_1$ (having a molecular weight higher than 1,000,000), fraction $F_2$ (having a molecular weight of 100,000 to 1,000,000 ) and fraction $F_3$ (having a molecular weight of 10,000 to 100,000 ). These fractions were freeze-dried to obtain white powder. The yield was about 450 mg of $F_1$, about 700 mg of $F_2$ and about 500 mg of $F_3$, respectively.

EXAMPLE 5

The procedures of Example 1 were repeated in the same manner except that *Leuconostoc mesenteroides* subsp. dextranicum, 46-1 (FERM BP-2670) was used instead of *Leuconostoc mesenteroides* subsp. dextranicum, BL-75 (FERM BP-2242), whereby 520 g of the RON substance in the form of a white powder was obtained.

EXAMPLE 6

The procedures of Example 1 were repeated in the same manner except that *Leuconostoc mesenteroides* subsp. dextranicum, NCFB 517 (FERM BP-2711) was used instead of *Leuconostoc mesenteroides* subsp. dextranicum, BL-75 (FERM BP-2242), whereby 99 g of the RON substance in the form of a white powder was obtained.

EXAMPLE 7

The procedures of Example 1 were repeated in the same manner except that *Leuconostoc mesenteroides* subsp. dextranicum, NCFB 531 (FERM BP-2712) was used instead of *Leuconostoc mesenteroides* subsp. dextranicum, BL-75 (FERM BP-2242), whereby 6 g of the RON substance in the form of a white powder was obtained.

EXAMPLE 8

The procedures of Example 1 were repeated in the same manner except that *Leuconostoc mesenteroides* subsp. dextranicum, NCFB 861 (FERM BP-2713) was used instead of *Leuconostoc mesenteroides* subsp. dextranicum, BL-75 (FERM BP-2242), whereby 3 g of the RON substance in the form of a white powder was obtained.

EXAMPLE 9

The procedures of Example 1 were repeated in the same manner except that *Leuconostoc mesenteroides* subsp. dextranicum, NCFB 864 (FERM BP-2714) was used instead of *Leuconostoc mesenteroides* subsp. dextranicum, BL-75 (FERM BP-2242), whereby 85 g of the RON substance in the form of a white powder was obtained.

EXAMPLE 10

The procedures of Example 1 were repeated in the same manner except that *Leuconostoc mesenteroides* subsp. dextranicum, NCFB 880 (FERM BP-2715) was used instead of *Leuconostoc mesenteroides* subsp. dextranicum, BL-75 (FERM BP-2242), whereby 123 g of the RON substance in the form of a white powder was obtained.

EXAMPLE 11

The procedures of Example 1 were repeated in the same manner except that *Leuconostoc mesenteroides* subsp. dextranicum, ATCC 1956 was used instead of *Leuconostoc mesenteroides* subsp. dextranicum BL-75 (FERM BP-21242), whereby 171 g of the RON substance in the form of a white powder was obtained.

EXAMPLE 12

The procedures of Example 1 were repeated in the same manner except that *Leuconostoc mesenteroides subsp. dextranicum, IFO* 3349 was used instead of *Leuconostoc mesenteroides* subsp. dextranicum, BL-75 (FERM BP-2242), whereby 108 g of the RON substance in the form of a white powder was obtained.

EXAMPLE 13

Culturing

Cells obtained by the stab culture of *Leuconostoc mesenteroides* subsp. dextranicum, BL-75 were inoculated into 8 ml of a culture medium (comprising 2.0% of sucrose, 0.5% of yeast extract and 2.0% of K$_2$HPO$_4$ and having a pH value of 7.4) charged in a test tube having a diameter of 15 mm. The stationary culture was carried out at 26° C. for 24 hours. Then, 8 ml of the culture broth was charged in an Erlenmeyer flask having a volume of 500 in which 400 ml of the culture medium having the same composition as described above was charged, and the stationary culture was carried out at 26° C. for 24 hours. Then, 40 g of sucrose were added to 400 ml of the culture liquid and the mixture was stirred to dissolve, and the culture was conducted at 30° C. for 24 hours.

Purification

After the pH value of the obtained culture broth was adjusted to 7, 400 ml of the culture broth was heated at 100° C. for the sterilization, after dilution of the culture broth for two times with water and the cells and insoluble substances were removed by a centrifugal separator to obtain 700 ml of a culture supernatant.

Methanol was gradually added to the obtained culture supernatant so that the final concentration was 40% (v/v), and the mixture was allowed to stand still. The supernatant was removed by decantation and the obtained precipitate was washed with 60% (v/v) methanol. The precipitate was dissolved in 18 Z of deionized water, and precipitation with methanol and washing with 60% (v/v) methanol were carried out to obtain 60 g of a glutinous white precipitate. The precipitate was dissolved in 400 ml of deionized water, and the solution was spray-dried to obtain 10 g of a white powder of the RON substance.

EXAMPLE 14

Cells in the culture broth (400 ml) obtained in the same manner as described in Example 13 were pulverized by an ultrasonic pulverizer and insoluble substances were removed by a centrifugal separator to obtain 350 ml of a processed culture broth. Then, 40 g of sucrose was added to the obtained processed culture broth, and the mixture was stirred to dissolve sucrose. The solution was allowed to stand at 30° C. for 24 hours and diluted 2 times with water. Methanol was gradually added to dilution with stirring so that the final concentration was 40% (v/v), and the mixture was allowed to stand for a while. The supernatant was removed by decantation, and the obtained precipitate was washed with 60% (v/v) methanol. The precipitate was dissolved in 700 ml of deionized water, and precipitation with methanol and washing with 60% (v/v) were repeated, whereby a glutinous precipitate was obtained. The precipitate was dissolved in 400 ml of deionized water, and the solution was freeze-dried to obtain 12 g of a white powder of the RON substance.

EXAMPLE 15

The procedures of Example 14 were repeated in the same manner except that the culture broth was not pulverized by the ultrasonic pulverizer, whereby 13 g of a white powder of the RON substance was obtained.

EXAMPLE 16

The processed culture broth obtained by subjecting the culture broth to centrifugal separation in Example 15 was dialyzed at 4° C. overnight against 50 mM phosphate buffer having a pH value of 5.5. Other operations were same as those conducted in Example 15. As the result, 13.5 g of a white powder of the RON substance was obtained.

What is claimed is:

1. A process for the preparation of a biologically active polysaccharide RON substance which comprises
   (a) culturing a microorganism belonging to the genus Leuconostoc, which has an ability of producing a physiologically active polysaccharide RON substance, said microorganism being at least one strain of *Leuconostoc mesenteroides* subsp. dextranicum, said strain selected from the group consisting of strain BL-75 (FERM BP-2242), strain NCFB 517 (FERM BP-2711), strain NCFB 531 (FERM BP-2712), strain NCFB 861 (FERM BP-2713), strain NCBF 864 (FERM BP-2714), strain 46-1 (FERM BP-2670), to form a polysaccharide RON substance having the following properties:
   (1) form: the substance is a white amorphous powder having no taste and no smell;
   (2) solubility: the substance is soluble in water, but the solution becomes milky white and viscous when the concentration is elevated; the substance is soluble in formamide and dimethylsulfoxide, but the substance is insoluble in alcohols, acetone, benzene, ethyl acetate, hexane, chloroform and carbon tetrachloride;
   (3) pH of aqueous solution: the aqueous solution is neutral to weakly acidic;
   (4) constituent saccharide: the substance comprises solely glucose;
   (5) elementary analysis values: the substance comprises 44.0 to 45.0% of C and 6.1 to 6.3% of H;
   (6) structure: the substance is an α-1,6-glucan and comprises a small amount of 3,6-branched side chains;
   (7) proteins: the substance comprises almost no proteins;
   (8) molecular weight: the substance does not permeate through a dialysis membrane and the molecular weight is presumed to be higher than 10,000 daltons;
   (9) specific rotation: $(\alpha)_D^{25} = +190° \sim +220°$ (C=0.5, formamide);
   (10) color reaction: the substance is positive to an anthrone sulfuric acid reaction and a phenol sulfuric acid reaction, but negative to a biurette reaction, the Lowry-Folin reaction, the Elson-Morgan reaction and an iodine reaction;
   (11) melting point: the substance has no definite melting point;
   (12) ultraviolet absorption spectrum: the substance has no characteristic absorption;
   (13) infrared absorption spectrum: the substance shows a characteristic absorption of α-glucan;
   (14) $^{13}$C-NMR spectrum: the substance shows characteristic chemical shift values of α-1,6-glucan in the main signals; and
   (15) biological activity: the substance has an antitumor activity against mice having a transplantable tumor, and
   (b) collecting said substance from a culture broth.

2. A process for the preparation of a biologically active polysaccharide RON substance which comprises
   (a) causing sucrose to act on a processed culture broth of a microorganism belonging to the genus Leuconostoc, said microorganism being at least one strain of Leuconostoc mesenteroides subsp. dextranicum, said strain selected from the group consisting of strain BL-75 (FERM BP-2242), strain NCFB 517 (FERM BP-2711), strain NCFB 531 (FERM BP-2712), strain NCFB 861 (FERM BP-2713), strain NCBF 864 (FERM BP-2714), strain 46-1 (FERM BP-2670), to form a polysaccharide RON having the following properties:

(1) form: the substance is a white amorphous powder having no taste and no smell;

(2) solubility: the substance is soluble in water, but the solution becomes milky white and viscous when the concentration is elevated; the substance is soluble in formamide and dimethylsulfoxide, but the substance is insoluble in alcohols, acetone, benzene, ethyl acetate, hexane, chloroform and carbon tetrachloride;

(3) pH of aqueous solution: the aqueous solution is neutral to weakly acidic;

(4) constituent saccharide: the substance comprises solely glucose;

(5) elementary analysis values: the substance comprises 44.0 to 45.0% of C and 6.1 to 6.3% of H;

(6) structure: the substance is an $\alpha$-1,6-glucan and comprises a small amount of 3,6-branched side chains;

(7) proteins: the substance comprises almost no proteins;

(8) molecular weight: the substance does not permeate through a dialysis membrane and the molecular weight is presumed to be higher than 10,000 daltons;

(9) specific rotation: $(\alpha)_D^{25} = +190° \sim +220°$ (C=0.5, formamide);

(10) color reaction: the substance is positive to an anthrone sulfuric acid reaction and a phenol sulfuric acid reaction, but negative to a biurette reaction, the Lowry-Folin reaction, the Elson-Morgan reaction and an iodine reaction;

(11) melting point: the substance has no definite melting point;

(12) ultraviolet absorption spectrum: the substance has no characteristic absorption;

(13) infrared absorption spectrum: the substance shows a characteristic absorption of $\alpha$-glucan;

(14) $^{13}$C-NMR spectrum: the substance shows characteristic chemical shift values of $\alpha$-1,6-glucan in the main signals; and (15) biological activity: the substance has an antitumor activity against mice having a transplantable tumor, and (b) collecting said substance.

3. The process for producing a biologically active polysaccharide RON substance according to claim 1, wherein the microorganism having an ability of producing the physiologically active polysaccharide RON substance is *Leuconostoc mesenteroides* subsp. dextranicum of a strain selected from the group consisting of strain BL-75 (FERM BP-2242) and strain 46-1 (FERM BP-2670).

4. The process for producing a biologically active polysaccharide RON substance according to claim 2, wherein the microorganism having an ability of producing the physiologically active polysaccharide RON substance is *Leuconostoc mesenteroides* subsp. dextranicum of a strain selected from the group consisting of strain BL-75 (FERM BP-2242) and strain 46-1 (FERM BP-2670).

5. The process for producing a biologically active polysaccharide RON substance according to claim 1, wherein the culturing is conducted at a temperature of 15° to 45° C. and at a pH of 5 to 7.

6. The process for producing a biologically active polysaccharide RON substance according to claim 2, wherein the process is conducted at a temperature of 15° to 45° C. and at a pH of 5 to 7.

7. The process for producing a biologically active polysaccharide RON substance according to claim 1, wherein the culturing is conducted at a temperature of 20° to 30° C., a pH of 5 to 7 and for a time period of 5 to 96 hours.

8. The process for producing a biologically active polysaccharide RON substance according to claim 2, wherein the process is conducted at a temperature of 20° to 30° C., a pH of 5 to 7 and for a time period of 5 to 96 hours.

9. The process for producing a biologically active polysaccharide RON substance according to claim 1, wherein the tumor is selected from the group consisting of syngeneic Meth-A tumor, Lewis lung carcinoma, Melanoma B-16, Sarcoma-180 and Erlich ascites tumor.

10. The process for producing a biologically active polysaccharide RON substance according to claim 2, wherein the tumor is selected from the group consisting of syngeneic Meth-A tumor, Lewis lung carcinoma, Melanoma B-16, Sarcoma-180 and Erlich ascites tumor.

11. The process for producing a biologically active polysaccharide RON substance according to claim 7, wherein the culturing is conducted in the presence of a nitrogen source selected from the group consisting of yeast extract, peptone, gluten meal, soybean powder, corn steep liquor, dry yeast, meat extract, ammonium sulfate and urea and an inorganic substance selected from the group consisting of phosphoric acid salts, magnesium salts, manganese salts, iron salts, cobalt salts and sodium salts.

12. A biologically pure culture of microorganism, *Leuconostoc mesenteroides* subsp. dextranicum strain BL-75 (FERM BP-2242) or strain 46-1 (FERM BP-2670).

13. A biologically pure culture of claim 12, wherein said microorganism is *Leuconostoc mesenteroides* subsp. dextranicum strain BL-75 (FERM BP-2242).

14. A biologically pure culture of claim 12, wherein said microorganism is *Leuconostoc mesenteroides* subsp. dextranicum strain BL-46-1 (FERM BP-2670).

* * * * *